(12) United States Patent
Balwalli-Udyawer et al.

(10) Patent No.: US 12,376,714 B2
(45) Date of Patent: Aug. 5, 2025

(54) PORTABLE CASING FOR SANITARY PRODUCTS

(71) Applicants: Shruti Balwalli-Udyawer, North Brunswick, NJ (US); Vikram Agrahar, Penn Wynne, PA (US)

(72) Inventors: Shruti Balwalli-Udyawer, North Brunswick, NJ (US); Vikram Agrahar, Penn Wynne, PA (US)

( * ) Notice: Subject to any disclaimer, the term of this patent is extended or adjusted under 35 U.S.C. 154(b) by 258 days.

(21) Appl. No.: 17/396,093

(22) Filed: Aug. 6, 2021

(65) Prior Publication Data

US 2022/0039616 A1    Feb. 10, 2022

Related U.S. Application Data

(60) Provisional application No. 63/063,756, filed on Aug. 10, 2020.

(51) Int. Cl.
| | |
|---|---|
| *A47K 10/42* | (2006.01) |
| *A61K 8/34* | (2006.01) |
| *A61Q 17/00* | (2006.01) |
| *B65D 25/20* | (2006.01) |
| *B65D 83/08* | (2006.01) |

(52) U.S. Cl.
CPC .............. *A47K 10/421* (2013.01); *A61K 8/34* (2013.01); *A61Q 17/005* (2013.01); *B65D 25/20* (2013.01); *B65D 83/0823* (2013.01)

(58) Field of Classification Search
CPC ...... A47K 10/421; A47K 8/34; A61Q 17/005; B65D 25/20; B65D 83/0823

USPC ..................................... 221/229, 231, 259, 1
See application file for complete search history.

(56) References Cited

U.S. PATENT DOCUMENTS

| | | | | |
|---|---|---|---|---|
| 274,400 | A * | 3/1883 | Soper ..................... | B65D 83/10 221/228 |
| 355,207 | A * | 12/1886 | Reinfeld ................ | A45C 11/18 206/39.5 |
| 599,821 | A * | 3/1898 | Adkins ................... | A45C 11/18 221/231 |
| 806,985 | A * | 12/1905 | Mallory ................. | A45C 11/18 206/39.5 |
| 1,155,791 | A * | 10/1915 | Cabell .................... | A45C 11/18 206/39 |
| 1,244,338 | A * | 10/1917 | Johnson ................. | B65D 83/10 221/232 |
| 2,216,476 | A * | 10/1940 | Mutz .................... | B65D 83/766 221/250 |
| 2,613,806 | A * | 7/1946 | Testi ..................... | B65D 83/10 221/229 |

(Continued)

FOREIGN PATENT DOCUMENTS

| | | | | |
|---|---|---|---|---|
| DE | 202012001362 U1 * | 6/2012 | ............. | B65D 25/20 |
| EP | 1533248 A1 * | 5/2005 | ......... | B65D 83/0829 |

(Continued)

*Primary Examiner* — Rakesh Kumar
(74) *Attorney, Agent, or Firm* — Offit Kurman; Tod A. Kupstas

(57) ABSTRACT

A portable casing is adapted to retain sanitary products. The portable casing has a retaining tray that is adapted be slid from the housing of the portable casing to permit sanitary products to be placed within the storage area. The retaining tray has a cut-out region that permits easy access to the sanitary products through a slot boated in a side of the portable casing.

19 Claims, 8 Drawing Sheets

(56) References Cited

U.S. PATENT DOCUMENTS

| | | | | |
|---|---|---|---|---|
| 2,675,909 | A * | 4/1954 | Auerbach | B65D 83/10 206/355 |
| 2,973,882 | A * | 3/1959 | Jeffus | B65D 83/0829 221/270 |
| 2,946,482 | A * | 7/1960 | Johnson | A47K 10/20 221/268 |
| 3,276,622 | A * | 10/1966 | Krzyzanowski | A47K 10/421 221/37 |
| 3,650,433 | A * | 3/1972 | Robertson | B65D 83/0823 221/65 |
| 4,071,165 | A * | 1/1978 | Leopoldi | B42F 7/10 271/42 |
| 4,170,914 | A * | 10/1979 | Carrier | B65D 83/0864 225/53 |
| 4,379,514 | A * | 4/1983 | Joffe | B65D 83/10 221/287 |
| 4,707,941 | A * | 11/1987 | Eastman | F41A 9/68 42/87 |
| 4,826,042 | A * | 5/1989 | Vujovich | B65D 83/10 206/355 |
| 4,887,739 | A * | 12/1989 | Parker | B65D 83/12 221/244 |
| 5,125,505 | A * | 6/1992 | Kurosaki | G09F 3/18 206/556 |
| 5,186,464 | A * | 2/1993 | Lamle | A63F 1/14 273/148 A |
| 5,609,252 | A * | 3/1997 | Koch | A47G 1/06 206/455 |
| 5,687,876 | A * | 11/1997 | Lucas, Jr. | A47J 31/08 221/36 |
| D396,978 | S * | 8/1998 | Kaiser | D6/518 |
| 6,182,860 | B1 * | 2/2001 | Ruhl | A47K 5/08 206/39 |
| 6,230,879 | B1 * | 5/2001 | Lin | B65D 83/0829 206/39.4 |
| 6,341,710 | B1 * | 1/2002 | Danielson | B65D 83/04 220/345.3 |
| 7,040,505 | B2 * | 5/2006 | Hashimoto | B65B 5/103 221/265 |
| 7,857,022 | B2 * | 12/2010 | Kraml | A45C 11/182 150/147 |
| 9,125,465 | B2 * | 9/2015 | Beckley | A45C 11/182 |
| 9,302,844 | B1 * | 4/2016 | Gringer | B65D 83/10 |
| 11,246,388 | B2 * | 2/2022 | Mayer | A45C 11/182 |
| 2008/0087560 | A1 * | 4/2008 | Kelly | A61B 7/02 206/229 |
| 2008/0264828 | A1 * | 10/2008 | Benson | A61F 13/5511 206/776 |
| 2011/0233229 | A1 * | 9/2011 | Schekalla | B65D 83/10 221/270 |
| 2014/0374430 | A1 * | 12/2014 | Meier | G07F 11/04 221/1 |
| 2016/0257482 | A1 * | 9/2016 | Gringer | B65D 83/0817 |
| 2022/0039616 | A1 * | 2/2022 | Balwalli-Udyawer | A47K 10/421 |

FOREIGN PATENT DOCUMENTS

| | | | | |
|---|---|---|---|---|
| FR | 2893233 A1 * | 5/2007 | | A45C 11/18 |
| WO | WO-2007057364 A1 * | 5/2007 | | A45C 11/18 |

* cited by examiner

PORTABLE CASING FOR SANITARY PRODUCTS

This application claims the benefit of U.S. Provisional Application Ser. No. 63/063,756, filed Aug. 10, 2020, the contents of which are incorporated herein by reference.

BACKGROUND

1. Field

This application is directed to the field of sanitary accessories. In particular, the application is directed to a portable casing for holding wipes used for sanitary purposes.

2. Description of the Related Art

In certain environments having a sanitary product, such as an alcohol-based wipe, or a wipe having other antimicrobial properties, is needed to sanitize the environment. However, frequently, unless one has a satchel or other device that is sized to carry a packet of such wipes, the availability of such wipes is lacking.

Therefore, there remains a need in the field to have ready access to such sanitary products.

SUMMARY

Briefly described, aspects of the present disclosure relate to portable casings adapted to dispense sanitary products.

An aspect of the present disclosure is a portable casing for sanitary products. The portable casing for sanitary products comprising: a housing; a storage area formed within the housing, wherein the storage area is adapted to retain sanitary products; an opening formed in a side of the housing; and a retention tray adapted to slide through the opening formed in the side of the housing, wherein when the retention tray slides through the opening formed in the side of the housing, access to the storage area is provided, wherein when the retention tray is located within the housing, access to the storage area is provided via the opening formed in the side of the housing and a cut-out formed in the retention tray.

Another aspect of the present disclosure is a portable casing. The portable casing comprising: a housing; a storage area formed by the housing, wherein the storage area has sanitary products stored therein; an opening formed in a side of the housing; and a retention tray adapted to slide through the opening formed in the side of the housing, wherein when the retention tray slides through the opening formed in the side of the housing, access to the storage area is provided, wherein when the retention tray is located within the housing, access to the storage area is provided via the opening formed in the side of the housing and a cut-out formed in the retention tray.

Still yet another aspect of the present disclosure is a method for dispensing a sanitary product. The method for dispensing a sanitary product comprising; accessing the sanitary product via a portable casing, the portable casing comprising; a housing; a storage area formed by the housing, wherein the storage area has sanitary products stored therein; an opening formed in the housing; a retention tray adapted to slide through the opening formed in the side of the housing, wherein when the retention tray slides through the opening formed in the side of the housing, access to the storage area is provided, wherein when the retention tray is located within the housing, access to the storage area is provided via the opening formed in the side of the housing and a cut-out formed in the retention tray; and removing the sanitary product.

DETAILED DESCRIPTION

To facilitate an understanding of embodiments, principles, and features of the present disclosure, they are disclosed hereinafter with reference to implementation in illustrative embodiments. Embodiments of the present disclosure, however, are not limited to use in the described systems or methods and may be utilized in other systems and methods as will be understood by those skilled in the art.

The components described hereinafter as making up the various embodiments are intended to be illustrative and not restrictive. Many suitable components that would perform the same or a similar function as the components described herein are intended to be embraced within the scope of embodiments of the present disclosure.

Figure 1:
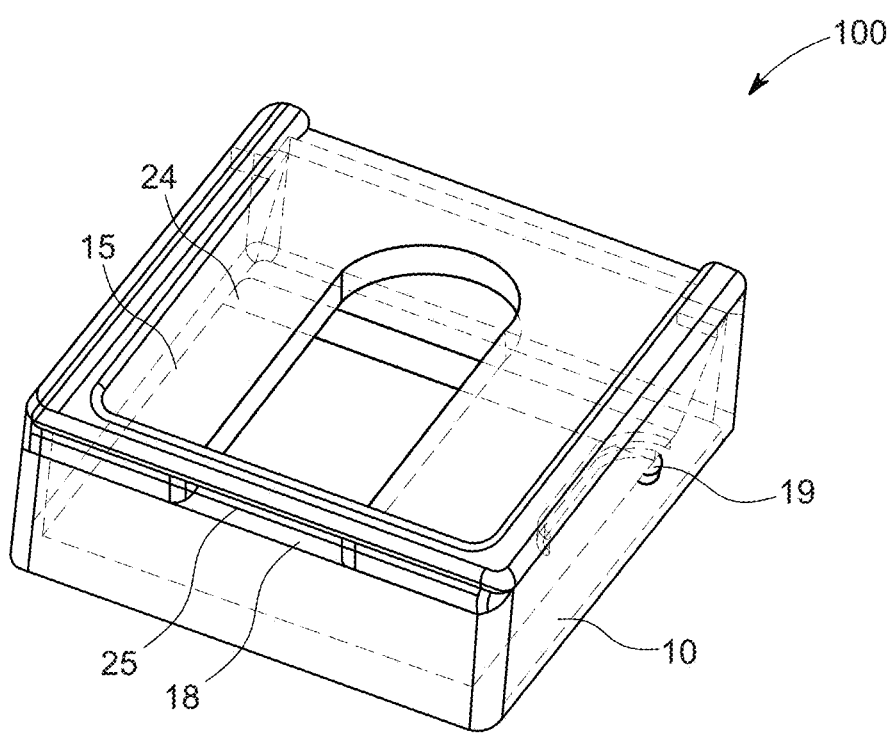
FIG. 1 is an isometric view of a portable casing.
Figure 2:
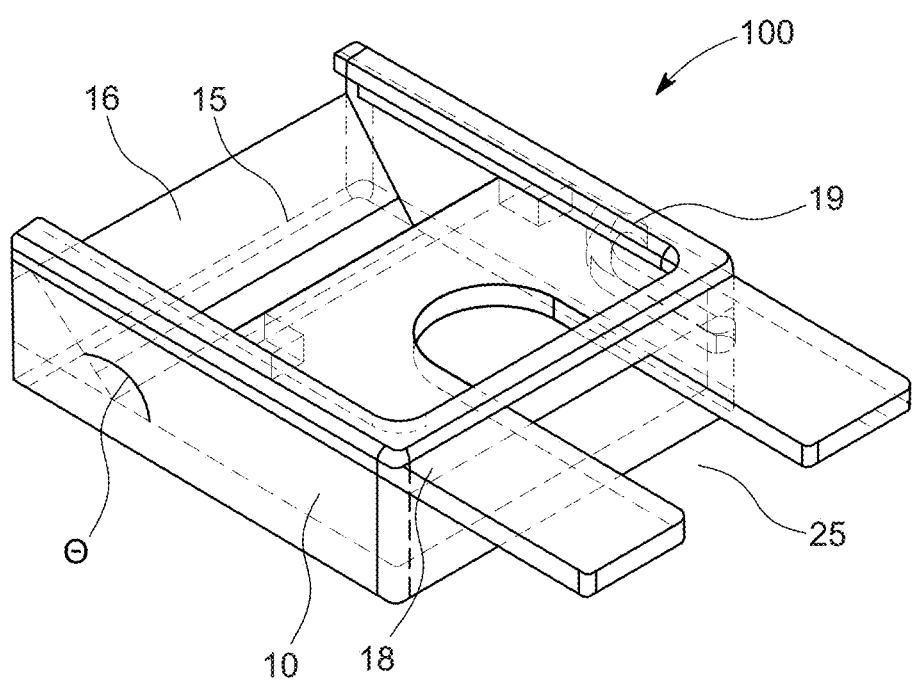
FIG. 2 is a view of the portable casing with its retention tray extended.
Figure 3:
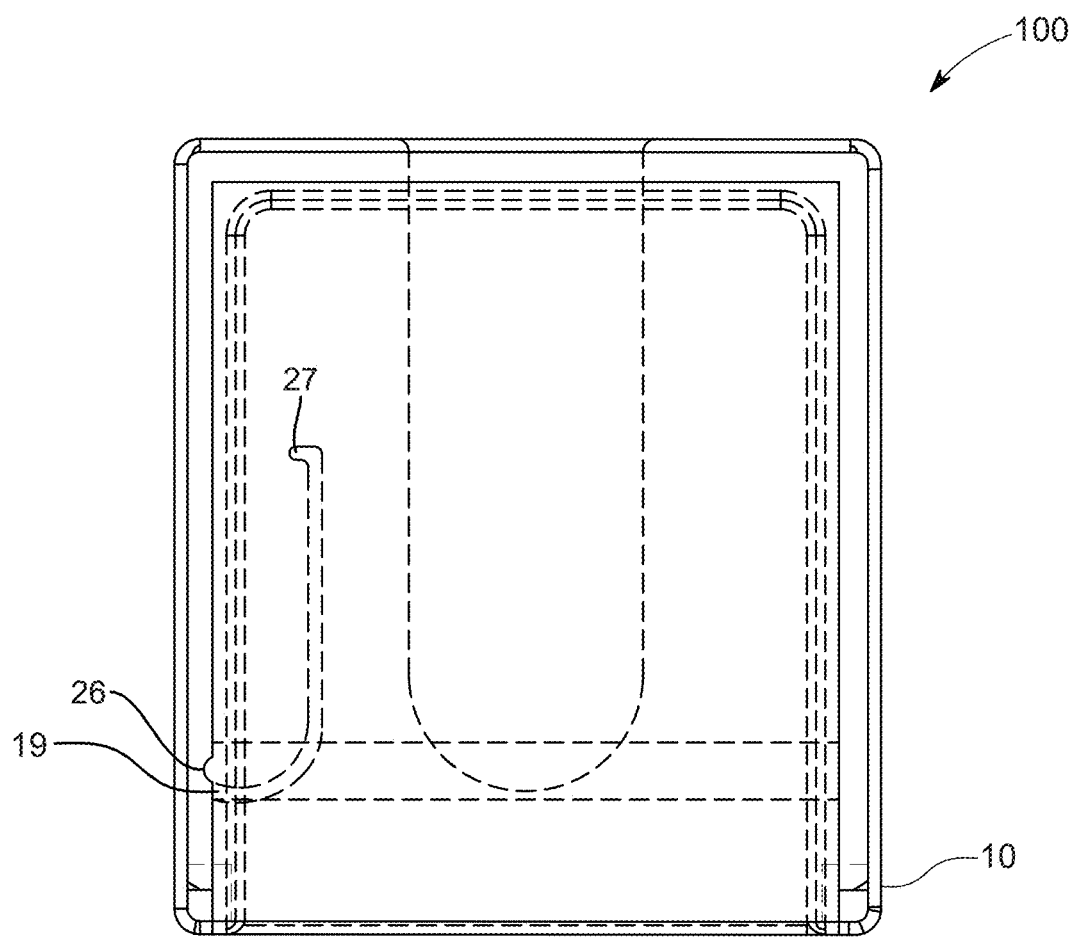
FIG. 3 is a bottom up view of the portable casing.
Figure 4:
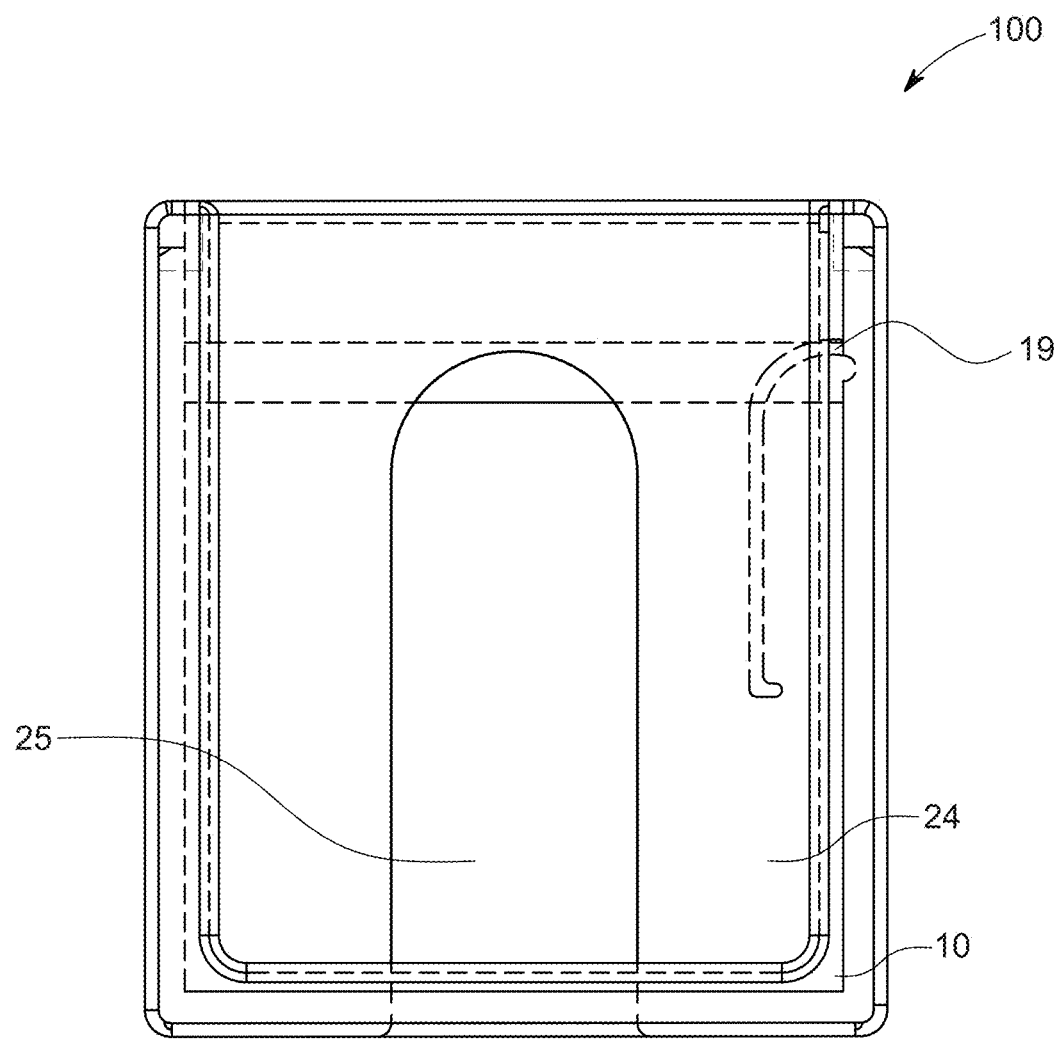
FIG. 4 is a top down view of the portable casing.
Figure 5:
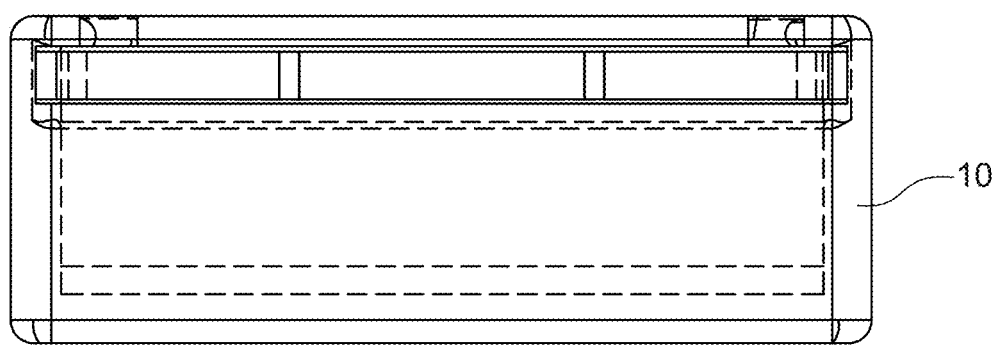
FIG. 5 is a side view of the portable casing.
Figure 6:
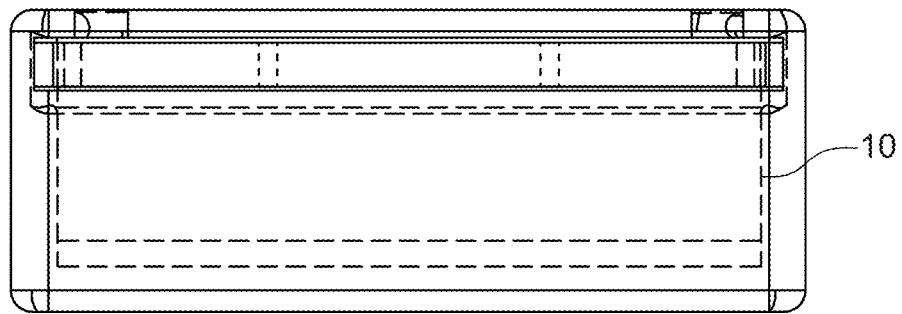
FIG. 6 is a view of the other side of the portable casing than that shown in FIG. 5.
Figure 7:
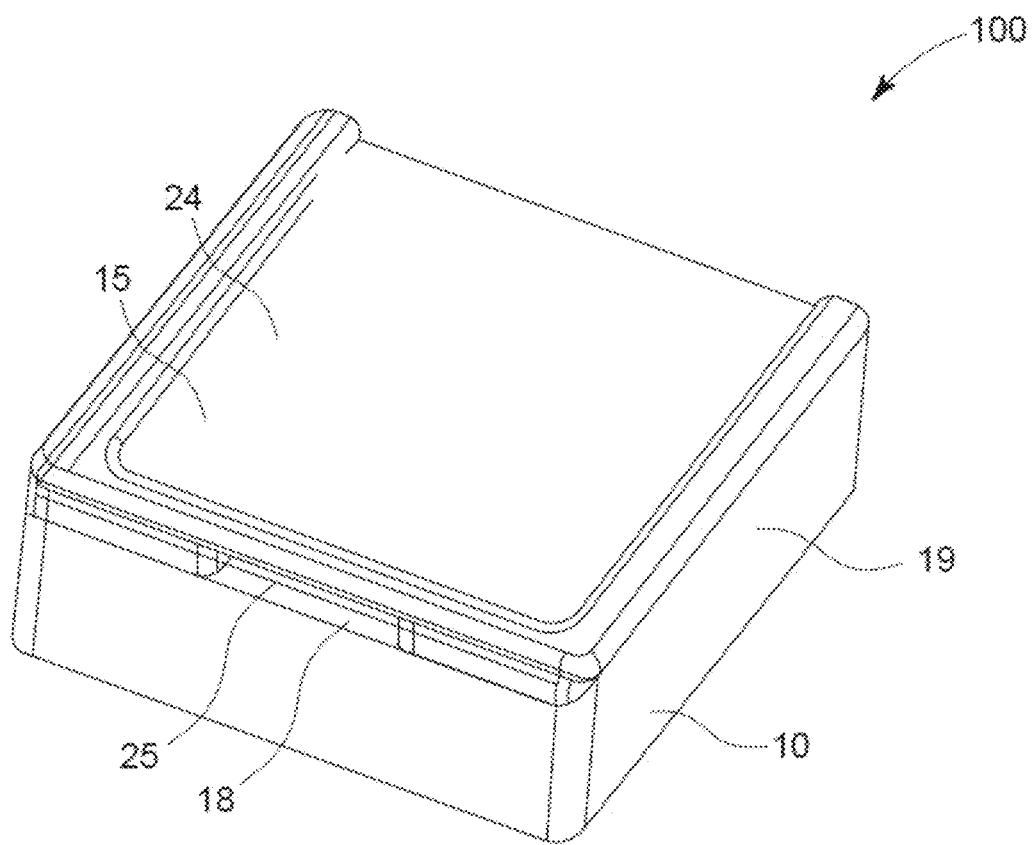
FIG. 7 is an isometric view of the portable casing shown in FIG. 1 with the broken lines removed.
Figure 8:
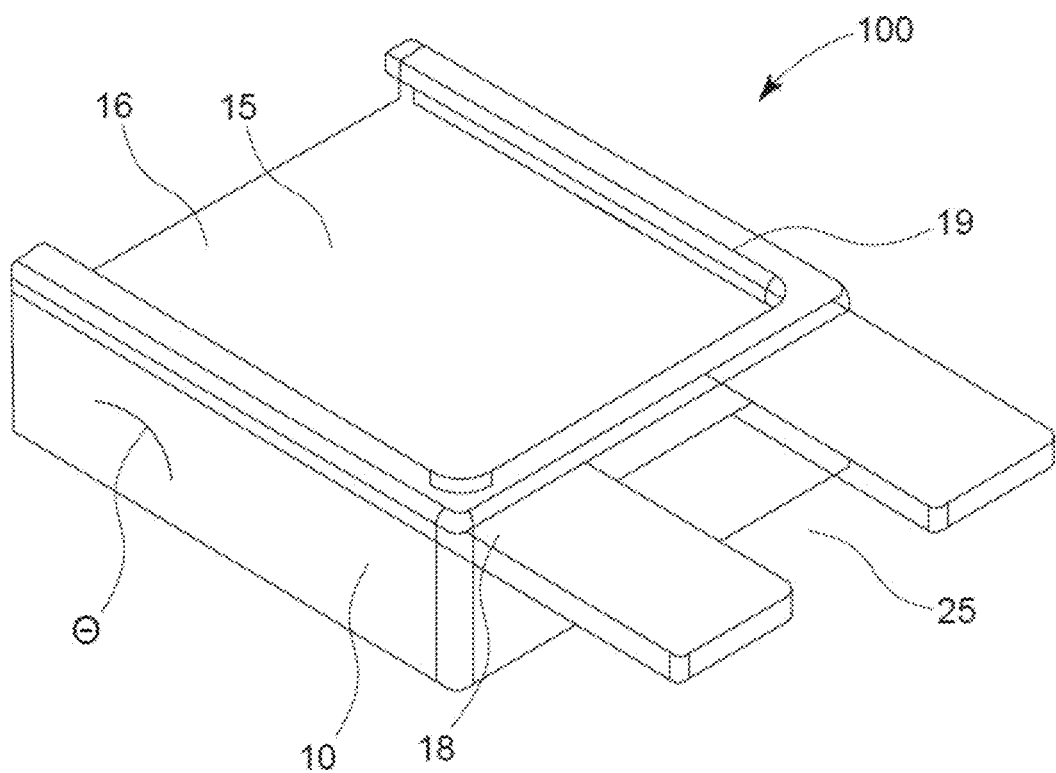
FIG. 8 is an isometric view of the portable casing with its retention tray extended as shown in FIG. 2 with the broken lines removed.

Now turning to FIGS. 1-6, FIG. 1 is an isometric view of a portable casing 100 adapted to store and dispense sanitary products. FIG. 2 is an isometric view of the portable casing 100 with a retention tray 24 extended. FIGS. 3-6 show different views of the portable casing 100 shown in FIGS. 1 and 2.

In an embodiment, the sanitary products are antimicrobial wipes. In an embodiment, the sanitary products are disinfectant wipes. In an embodiment, the sanitary products are alcohol swabs. In an embodiment, the sanitary products are antibacterial wipes. In an embodiment, the sanitary products are antiviral wipes. In an embodiment, the sanitary products are wipes that are adapted to effectively sterilize any surface with almost 100% efficiency. In an embodiment, the sanitary products are moisturizing wipes. In an embodiment, the sanitary products are wipes adapted to both disinfect and apply a topical cream. In an embodiment, the sanitary products are wipes adapted to treat wounds. In an embodiment, the sanitary products are wipes adapted to treat burns. In an embodiment, any product that has a shape and consistency of a wipe can be stored within portable casing 100.

In an embodiment, the portable casing 100 dispenses wipe-like products that are not primarily sanitary in nature. For example, in an embodiment, the portable casing 100 dispenses wipes used for removing make-up. In an embodiment, the portable casing 100 dispenses wipes used for applying make-up.

Still referring to FIG. 1, the portable casing 100 comprises a housing 10, a storage area 15, and a retention tray 24 that has a cut-out 25 formed therein. A slot 18 is formed in one wall of the housing 10.

The housing 10 may be made from a plastic material. In an embodiment, the housing 10 is made from a metallic material. In an embodiment, the housing 10 is made from an organic material. In an embodiment, the housing 10 is made from an alloy. In an embodiment, the housing 10 is made from a disposable material. In an embodiment, the housing 10 is made of ceramic material. In an embodiment, the housing 10 is made of organic material, such as bamboo or wood. In an embodiment, the housing 10 is made of a magnetic material. In an embodiment, the housing 10 is made of a composite of any of the above-mentioned materials.

The storage area 15 is formed from portions of the housing 10 that form the walls. In an embodiment, the storage area 15 is formed separately from the housing 10. In an embodiment, the storage area 15 is formed separately from the housing 10 and further has a humidity controlling component to control the amount of moisture within the storage area 15.

The storage area 15 is sized to contain sanitary products, such as alcohol wipes, that are placed therein. In an embodiment, the storage area 15 has at least one sloped portion 16. The sloped portion 16 is formed to facilitate the continued dispensation of sanitary wipes.

In an embodiment, the sloped portion 16 has an angle θ of 145 degrees. In an embodiment, the sloped portion 16 has an angle θ of 130 degrees. In an embodiment, the sloped portion 16 has an angle θ of 160 degrees. In an embodiment, the sloped portion 16 has an angle θ of 125 degrees. In an embodiment, the sloped portion 16 has an angle θ of 165 degrees. In an embodiment, the sloped portion 16 has an angle θ that is greater than 180 degrees. In an embodiment, the sloped portion 16 has an angle θ that is less than 90 degrees. In an embodiment, the sloped portion 16 has an angle θ greater than 0 degrees.

The storage area 15 may be adapted to retain loose wipes or alternatively may receive a packet or sub-container that is holds the product. In embodiment, the storage area 15 has a liner that is placed therein that is adapted to retain moisture. In an embodiment, the storage area 15 has a textured surface that is adapted to frictionally retain wipes. In an embodiment, the storage area 15 has an adhesive surface that is adapted to retain wipes.

The retention tray 24 is adapted to retain products within the storage area 15. The retention tray 24 has a cut-out 25 that is adapted to enable a user to take a product, such as a wipe, from the container area. In operation, product, such as wipes are placed within the storage area 15 by sliding the retention tray 24 in one direction through the slot 18. In FIG. 2, the retention tray 24 is slid towards the slot 18. The cut-out 25 in the retention tray 24 is located proximate to the slot 18 when located with the housing 10.

By sliding the retention tray 24 out though the slot 18, access to a storage area 15 is provided. The retention tray 24 is then slid back through the slot 18 and the product itself is accessed through the slot 18 and removal of the sanitary product is facilitated by the cut-out 25. While the slot 18 is shaped as a slot, openings with other shapes can be used to access products, such as circular, oval, square, etc.

In an embodiment, a notch 19 is formed in the retention tray 24. The notch 19 extends from one side of the retention tray 24, at a location wherein a retention tray protrusion 26 extends outwardly toward the housing, curves and extends parallel to the cut-out 25 formed in the retention tray 25. At a distal end of the notch 19 is a portion 27 that extends towards the side of the retention tray 24. The notch 19 prevents the retention tray from sliding out of the housing 10 by engaging with a portion of the housing 10.

In an embodiment, the cut-out 25 is located at another location than the one indicated in the figures, such as to the side or in the opposite direction of the cut-out 25 in FIGS. 1 and 2. In an embodiment, the cut-out 25 is U-shaped. In an embodiment, the cut-out is formed as a square shape. In an embodiment, the cut-out is formed as a semi-circle. In an embodiment, the cut-out is formed as a slit. It should further be understood that the cut-out is not necessarily cut out from the retention tray, but rather the retention tray 24 is formed in such a manner as to have a portion of the retention tray 24 removed.

In an embodiment, there is a biasing mechanism that facilitates removal of the product from the storage area 15. For example, the retention tray 24 or a bottom portion of the storage area 15 may be spring biased to either retain the sanitary products or to dispense the sanitary products.

In an embodiment, the portable casing 100 has means for retaining moisture within the portable casing 100 so that for those wipes that are designed to retain moisture, the moisture may be retained. In an embodiment, the material of the casing and the sealing of the portable casing 100 prevents excessive loss of fluid and the products retained within the casing 100 remain moist. In an embodiment, the portable casing 100 has a moisture dispensing reservoir located within the confines of the portable casing 100. In an embodiment, the moisture dispensing reservoir is adapted to be refillable so that moisture for the products can be replenished over time.

Preferably, attached to the housing 10, at one of the sides, is a mechanism for securing the portable casing 100 to a keychain. In an embodiment, the mechanism is attached to the top or to the bottom of the housing 10. In an embodiment, there is mechanism that permits the portable casing 100 to be secured to a stethoscope, such as a clip or a clasp. In an embodiment, there is a mechanism for securing the portable casing 100 to a pocket. In an embodiment, there is a mechanism for securing the portable casing 100 to a wallet or a purse. In an embodiment, there is mechanism for securing the portable casing 100 to an article of clothing. In an embodiment, the housing 10 of the portable casing 100 is magnetic and may be secured to an object, such as a refrigerator.

While embodiments of the present disclosure have been disclosed in exemplary forms, it will be apparent to those skilled in the art that many modifications, additions, and deletions can be made therein without departing from the spirit and scope of the invention and its equivalents, as set forth in the following claims.

What is claimed is:

1. A portable casing for sanitary products comprising:
   a housing having a side;
   a storage area formed within the housing, wherein the storage area is adapted to retain sanitary products;
   a slot formed in the side of the housing; and
   a retention tray adapted to slide through the slot formed in the side of the housing, wherein when the retention tray slides through the slot formed in the side of the housing, access to the storage area is provided, wherein when the retention tray is located within the housing, access to the storage area is provided via the slot formed in the side of the housing and a cut-out formed in the retention tray, and
   wherein the retention tray has a notch formed therein, wherein the notch extends from one side of the retention tray, at a location wherein a retention tray protrusion extends outwardly toward the housing, the notch curves, and further extends parallel in a lengthwise direction to the cut-out formed in the retention tray, wherein at a distal end of the notch there is a portion of the notch that extends perpendicularly to the parallel extending lengthwise direction of the notch and towards the one side of the retention tray.

2. The portable casing of claim 1, wherein the cut-out formed in the retention tray is U-shaped.

3. The portable casing of claim 1, further comprising sanitary products located within the storage area, wherein the cut-out formed in the retention tray is adapted to provide access to the sanitary products.

4. The portable casing of claim 1, further comprising sanitary products located within the storage area, wherein the sanitary products are wipes.

5. The portable casing of claim 4, wherein the wipes are anti-microbial wipes.

6. The portable casing of claim 4, wherein the wipes are alcohol swabs.

7. The portable casing of claim 1, further comprising a sloped portion formed on the bottom of the housing.

8. The portable casing of claim 1, wherein the sloped portion has an angle theta of 160 degrees.

9. A portable casing comprising:
    a housing having a side;
    a storage area formed by the housing, wherein the storage area has sanitary products stored therein;
    a slot formed in the side of the housing; and
    a retention tray adapted to slide through the slot formed in the side of the housing, wherein when the retention tray slides through the slot formed in the side of the housing, access to the storage area is provided, wherein when the retention tray is located within the housing, access to the storage area is provided via the slot formed in the side of the housing and a cut-out formed in the retention tray; and
    wherein the retention tray has a notch formed therein, wherein the notch extends from one side of the retention tray, at a location wherein a retention tray protrusion extends outwardly toward the housing, the notch curves, and further extends parallel in a lengthwise direction to the cut-out formed in the retention tray, wherein at a distal end of the notch there is a portion of the notch that extends perpendicularly to the parallel extending lengthwise direction of the notch and towards the one side of the retention tray.

10. The portable casing of claim 9, wherein the cut-out formed in the retention tray is U-shaped.

11. The portable casing of claim 9, wherein the sanitary products are wipes.

12. The portable casing of claim 11, wherein the wipes are anti-microbial wipes.

13. The portable casing of claim 11, wherein the wipes are alcohol swabs.

14. The portable casing of claim 9, further comprising a sloped portion formed on the bottom of the housing.

15. The portable casing of claim 9, wherein the sloped portion has an angle theta greater than 0 degrees.

16. A method for dispensing a sanitary product comprising;
    accessing the sanitary product via a portable casing, the portable casing comprising;
        a housing having a side;
        a storage area formed by the housing, wherein the storage area has sanitary products stored therein;
        a slot formed in the side of the housing;
        a retention tray adapted to slide through the slot formed in the side of the housing, wherein when the retention tray slides through the slot formed in the side of the housing, access to the storage area is provided, wherein when the retention tray is located within the housing, access to the storage area is provided via the slot formed in the side of the housing and a cut-out formed in the retention tray, wherein the retention tray has a notch formed therein, wherein the notch extends from one side of the retention tray, at a location wherein a retention tray protrusion extends outwardly toward the housing, the notch curves, and further extends parallel in a lengthwise direction to the cut-out formed in the retention tray, wherein at a distal end of the notch there is a portion of the notch that extends perpendicularly to the parallel extending lengthwise direction of the notch and towards the one side of the retention tray; and
    removing the sanitary product.

17. The method of claim 16, wherein the cut-out formed in the retention tray is U-shaped.

18. The method of claim 16, wherein the sanitary products are wipes.

19. The method of claim 18, wherein the wipes are alcohol swabs.

* * * * *